(12) United States Patent
Vagn-Erik

(10) Patent No.: US 7,320,556 B2
(45) Date of Patent: Jan. 22, 2008

(54) GRIPPING DEVICES

(76) Inventor: Dall Vagn-Erik, Key Cottage, 80 Portlock Road, Maidenhead, Berkshire SL6 6DZ (GB)

( * ) Notice: Subject to any disclaimer, the term of this patent is extended or adjusted under 35 U.S.C. 154(b) by 0 days.

(21) Appl. No.: 10/332,607

(22) PCT Filed: Jul. 11, 2001

(86) PCT No.: PCT/GB01/03118
§ 371 (c)(1),
(2), (4) Date: Oct. 3, 2003

(87) PCT Pub. No.: WO02/03868
PCT Pub. Date: Jan. 17, 2002

(65) Prior Publication Data
US 2004/0057789 A1 Mar. 25, 2004

(30) Foreign Application Priority Data
Jul. 11, 2000 (GB) .............................. 0017068.8
Oct. 16, 2000 (GB) .............................. 0025345.0

(51) Int. Cl.
*F16G 11/00* (2006.01)
(52) U.S. Cl. .................. 403/385; 403/389; 403/390; 403/396; 403/400; 600/227; 606/61
(58) Field of Classification Search ............... 403/389, 403/390, 398–400, 305, 306, 385, 396; 600/227, 600/230; 606/61; 24/500, 501, 515; 901/31, 901/39
See application file for complete search history.

(56) References Cited

U.S. PATENT DOCUMENTS 731,635 A * 6/1903 Vandegrift et al. ......... 403/299
1,712,108 A * 5/1929 Goeller ........................ 403/305
1,833,008 A * 11/1931 Thorpe ........................ 403/305

(Continued)

FOREIGN PATENT DOCUMENTS

EP    0-445-014 (A1)    2/1991

(Continued)

*Primary Examiner*—Daniel P. Stodola
*Assistant Examiner*—Michael P. Ferguson
(74) *Attorney, Agent, or Firm*—McDermott Will & Emery LLP

(57) ABSTRACT

A gripping device comprises a support body (2) within a sleeve (8), with the sleeve being mounted around the body for relative translational movement along a common axis thereof. A plurality of gripping elements (10, 12) are pivotally mounted in the body (2), the elements having lever arms (20, 22) projecting laterally from the boundary of the body. Translational movement of the sleeve (8) relative to the body (2) causes working engagement of the sleeve with the gripping element lever arms (20, 22), and movement of the lever arms to pivot the elements (10, 12) and close the elements around an item captured therebetween. Normally, the pivotal axes for the gripping elements (10, 12) are disposed within the support body (2), with the elements themselves projecting axially from an end thereof. The pivotal axes are normally substantialy parallel, and indeed the gripping elements may all be mounted for pivotal movement about the same common axis (18). The pivotal axis or axes will usually be perpendicular to the common axis of the support body and sleeve, but there may be applications in which a different angular relationship between these axes will be used.

17 Claims, 3 Drawing Sheets

U.S. PATENT DOCUMENTS

| | | | | |
|---|---|---|---|---|
| 3,100,324 | A | * | 8/1963 | Tutino et al. .................. 24/346 |
| 4,566,157 | A | * | 1/1986 | Packendorff .................. 24/536 |
| 5,606,782 | A | | 3/1997 | Patterson et al. |
| 5,810,819 | A | | 9/1998 | Errico et al. |
| 5,867,877 | A | * | 2/1999 | Patterson et al. .......... 24/598.5 |
| 6,171,311 | B1 | * | 1/2001 | Richelsoph .................. 606/61 |
| 6,371,957 | B1 | * | 4/2002 | Amrein et al. ................ 606/61 |

FOREIGN PATENT DOCUMENTS

| | | | |
|---|---|---|---|
| FR | 2 682 280 | * | 10/1991 |
| GB | 2 222 629 | * | 9/1990 |

* cited by examiner

GRIPPING DEVICES

This Application is a U.S. National filing under §371 of International Application No. PCT/GB01/03118, filed 11 Jul. 2001, claiming priority from British Appln. No. 0017068.8, filed 11 Jul. 2000 and British Appln. No. 0025345.0, filed 16 Oct. 2000, now pending (which are hereby incorporated by reference).

TECHNICAL FIELD

This invention relates to gripping devices, and has particular use in surgical applications. It is especially useful in applications where bones or bone elements require external fixation in situations where delicate adjustment is needed.

According to the invention, a gripping device comprises a support body within a sleeve, with the sleeve being mounted around the body for relative translational movement along a common axis thereof. A plurality of gripping elements are pivotally mounted in the body, the elements having lever arms projecting laterally from the boundary of the body. Translational movement of the sleeve relative to the body causes working engagement of the sleeve with the gripping element lever arms, and movement of the lever arms to pivot the elements and close the elements around an item captured therebetween. Normally, the pivotal axes for the gripping elements are disposed within the support body, with the elements themselves projecting axially from an end thereof. The pivotal axes are normally substantially parallel, and indeed the gripping elements may all be mounted for pivotal movement about the same common axis. The pivotal axis or axes will usually be perpendicular to the common axis of the support body and sleeve, but there may be applications in which a different angular relationship between these axes will be used. A mechanism is normally incorporated in the device for locking the gripping elements around a respective captured item.

In most embodiments of the invention, the gripping elements will have matching jaws for holding elongate components. Typically, three gripping elements will be used, two with jaws for engaging such component at spaced sections therealong, and one with a jaw for engaging the component at an intermediate section.

There are various means for accomplishing the relative translational movement between the support body and the sleeve. One such mechanism comprises complementary screw threads in permanent mesh, rotation of the sleeve around the body effecting the requisite movement. However, as such rotational movement can be rather cumbersome in the circumstances of a surgical operation, in preferred embodiments of the invention a more direct frictional mechanism is employed. For example, if the support body is a tight fit in the sleeve, and there is frictional contact between the engaging surfaces, with an item loosely captured between the gripping elements, the support body can be pushed into the sleeve against the frictional resistance, to engage the gripping element around the captured item. In many applications simple friction can be sufficient to hold the support body against accidental or unintentional withdrawal, but the frictional engagement can be enhanced by having some resilient flexibility in one or other of the support body and sleeve. This can easily be accomplished by the use of a split sleeve, enabling the sleeve to expand slightly as the support body is pressed into it. In a more sophisticated arrangement, the support body and sleeve are formed with matching peripheral teeth which are normally in mesh. Once again, a degree of flexibility is provided in one or both of the support body and sleeve, which enables the teeth on one surface to ride the teeth on the other as the support body is pressed into the sleeve to close the gripping elements. The result is a ratchet effect with the support body being locked in place within the sleeve when the gripping elements are fully closed around a captured item. Once again, the requisite resilience may be provided by forming the sleeve as a split sleeve, although multiple splits extending into only part of the length of the sleeve can provide more uniform circumferential resistance, and progressively increasing resistance as the support body enters further into the sleeve.

SUMMARY OF THE INVENTION

The working engagement between the gripping element lever arms and the sleeve is normally at the end face of the sleeve, which does of course facilitate the use of a screw thread between the sleeve and the support body. However, the gripping element lever arms can in some variants engage walls of openings, slots or recesses in the sleeve. An arrangement in which the lever arms are received in openings in the sleeve can be of additional value when there is a need for the gripping elements to be positively withdrawn, rather than merely released or withdrawn by some resilient force.

In another preferred aspect of the invention provision is made for means by which the activation of the gripping devices can be facilitated. A liner can be interposed between the inner surface of the sleeve and the juxtaposed outer surface of the support body, with the liner being fixed axially relative to one of the sleeve and support body. The liner is adjustable to selectively engage the other of the sleeve and support body, to hold the body axially in the sleeve. The adjustment of the liner is preferably resilient; ie, some means is provided for deforming the liner to withdraw it from engagement, the means being releasable to allow the liner to resiliently engage the other of the sleeve and body to hold the body axially in the sleeve.

Normally, the overall cross-section of the support body and sleeve in the variant just described is substantially circular, but other shapes can certainly be used while still benefiting from the invention. The liner is typically a split collar, the jaws of which can be moved towards or away from each other to grip a body within the collar or respectively expand the collar into engagement with the sleeve. In a preferred arrangement, the liner is a collar mounted in an annular groove on the support body which in its normal state presses outwardly against the sleeve.

Devices according to the invention and including a liner as described above will normally include a mechanism for adjusting the liner, and typically the adjustment mechanism comprises one or more pins extending through the wall of the sleeve. Where the device is of an overall cylindrical or tubular construction, the pins will normally extend tangentially relative thereto. Of course, if the liner is mounted on the support body, then the locking mechanism must permit axial movement of the liner relative thereto. For this purpose then, the pins will normally engage one or more axially extending surfaces or walls on the liner. Of course, one jaw of a split collar can have its circumferential location on one or both of the support body and sleeve effectively fixed, with all relevant adjustment being inducted relative to the other jaw.

Roughened surfaces are referred to above for enhancing the locking engagement to hold the body axially in the sleeve. Such surfaces can also be used when a liner is included. Flexible peripheral teeth can be employed, but it is preferred to form the relevant surfaces with complementary annular grooves. The grooved surfaces are preferably inclined saw tooth in cross-section, to permit axial movement of the support body in the sleeve whereby the teeth on one surface can ride the teeth on the other during said axial movement, preferentially in the direction corresponding to the translational movement required to pivot the gripping elements.

BRIEF DESCRIPTION OF THE DRAWINGS

The invention will now be described by way of example and with reference to the accompanying drawings, wherein.

DETAILED DESCRIPTION

Figure 1:
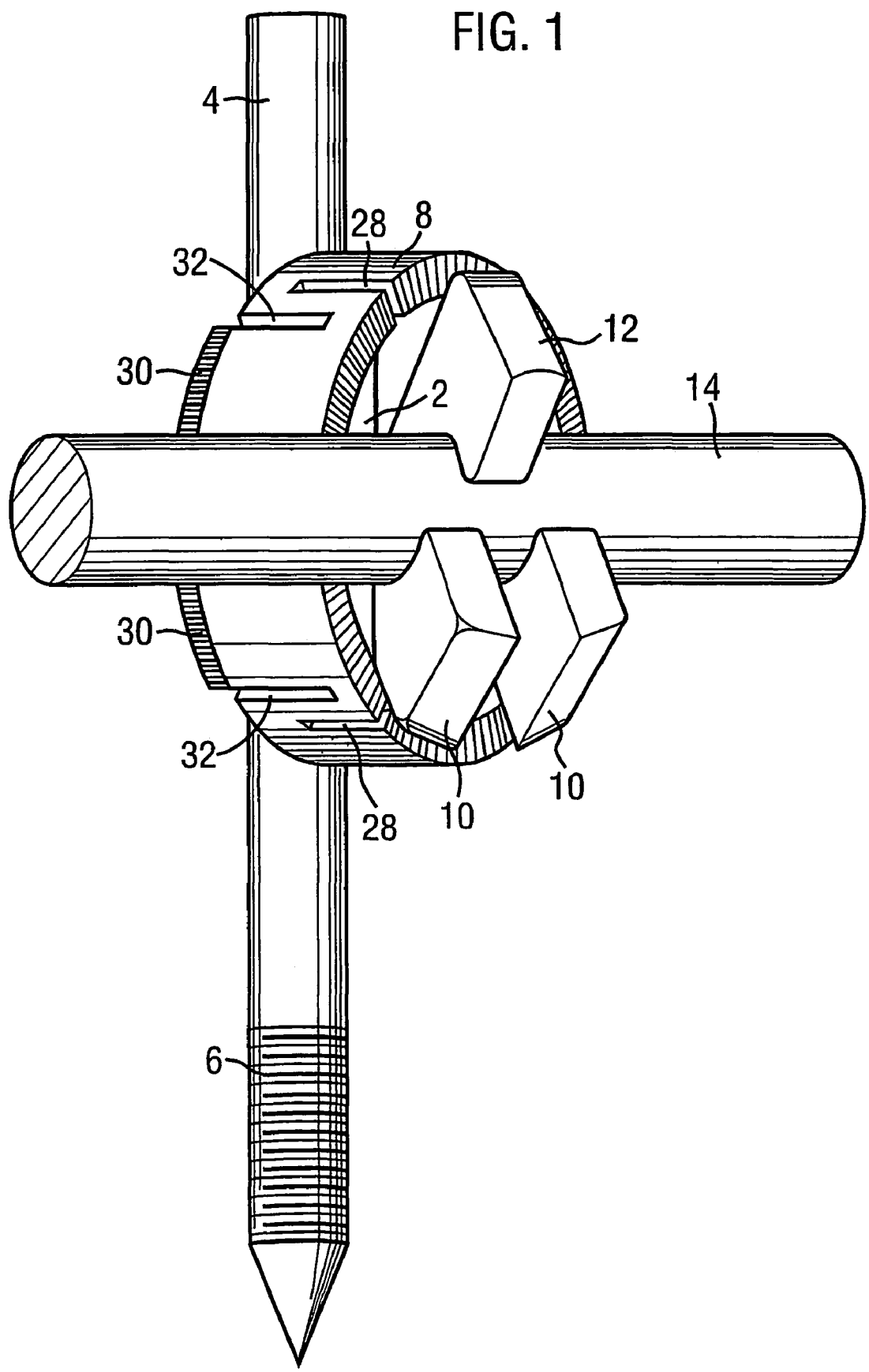
FIG. 1 is a perspective view of a device according to a first embodiment of the invention mounted on a shaft, and gripping a connecting rod.

In FIG. 1 a support body 2 is fixedly mounted on shaft 4 which, as shown, is sharpened at one end and formed with a threaded section 6. Such a shaft might be a cortical bone screw forming part of an external fixation mechanism in a surgical repair. The support body 2 is enclosed within a sleeve 8 from which apparently project gripping elements 10 and 12, to hold a rod 14. The assembly of the support body, sleeve and gripping elements will be readily apparent from FIG. 2.

Figure 2:
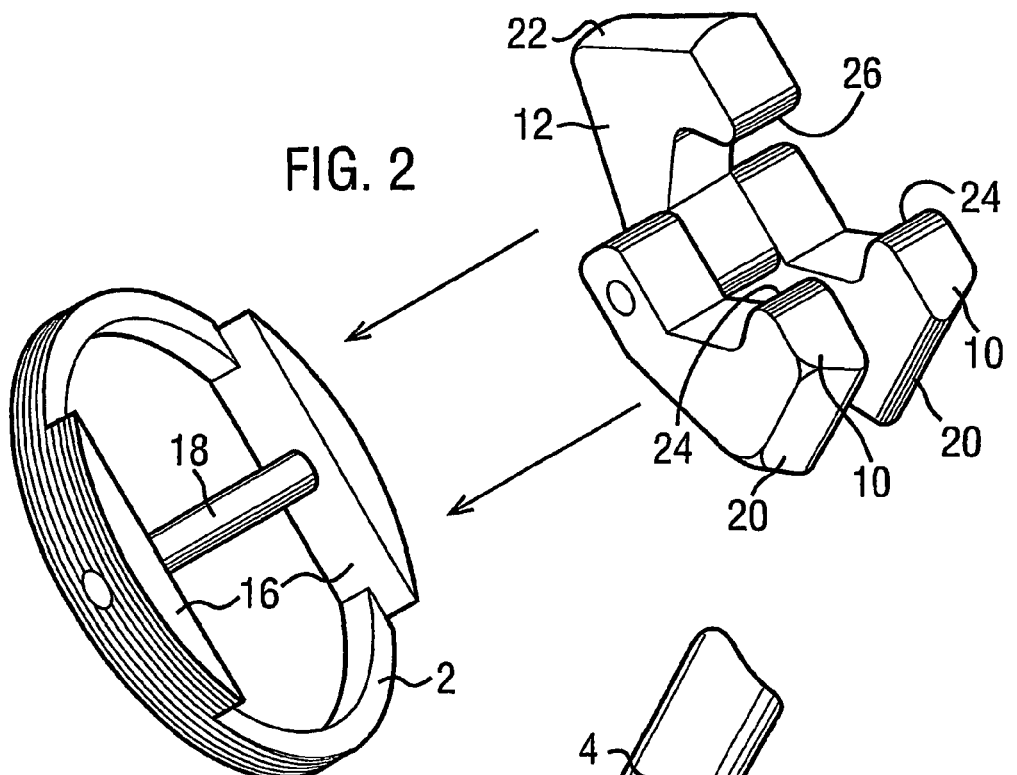
FIG. 2 is an exploded perspective view of the support body in the device shown in FIG. 1, and the respective gripping elements.

The support body shown in FIG. 2 is essentially an annulus with diametrically opposed enlarged sections 16 between which extends a pivot axle 18. Gripping elements 10 and 12 are mounted on the pivot axle 18. When mounted on the pivot axle, lever arms 20 and 22 project beyond the lateral boundary of the support body. The support body 2 is formed with peripheral serrations or teeth, and complementary serrations or teeth are formed on the internal surface of the sleeve 8. The sleeve is partially split at spaced locations 28, to provide some resilient flexibility. This enables the support body 2 to be pressed into the sleeve with the respective teeth or serrations riding over each other. Such movement eventually results in the end face of the sleeve engaging the lever arms, causing the gripping elements to pivot about the axial 18, and as a consequence, the jaws 24, 26 to close on for example, the rod 14. This situation will be achieved with the teeth or serrations once again in mesh, and the gripping of the rod 14 is therefore secure.

It will be appreciated that in the arrangement described above and provided the sleeve 8 has sufficient axial length, a support body 2 may be received in either end of the sleeve 8, thereby enabling the same gripping technique to hold two items to form a coupling therebetween. Thus, in the device of FIG. 1 the shaft 4 is held by gripping elements 30 on one side and a single further element (not shown) on the other side. Resilient flexibility is provided at that end of the sleeve 8 by part splits 32.

As noted above, the device of the invention has particular use in surgical applications, and in the external fixation of bone parts. Where the gripping element mechanism is used to secure the support body to both the rod and the shaft in the embodiment of FIG. 1, the invention enables both pivotal and translational movement of the rod and shaft relative to the support body until the exact desired positions have been achieved, at which point the respective gripping element sets can be tightened by the simple pressing of the support bodies into the respective sleeve ends. This is particularly advantageous, and this final step can be accomplished by the surgeon, as soon as the final positional adjustments have been made. The pressing step can itself be accomplished using electromagnetic clamps fitted to the various gripping devices. This enables all or some of the devices to be activated simultaneously and immediately when manipulation and positioning has been completed.

The gripping device of the invention has been described as consisting of essentially circular or cylindrical components. However, this does result in oblique engagement between the gripping elements and the end face of the sleeve during the translational movement of the support body relative to the sleeve. This minor problem can be alleviated by selecting appropriate profiles for the gripping elements at the points where they engage the sleeve, and/or forming ramps or steps at the end of the sleeve specifically aligned for engagement with the gripping elements. Such ramps or steps could be formed on a separate annulus rotatably mounted on the end face of the sleeve. In another alternative, the gripping elements could themselves be mounted on individual pivotal axles parallel with the relevant tangent at which the lever arms engage the end face of the sleeve.

Figure 3:
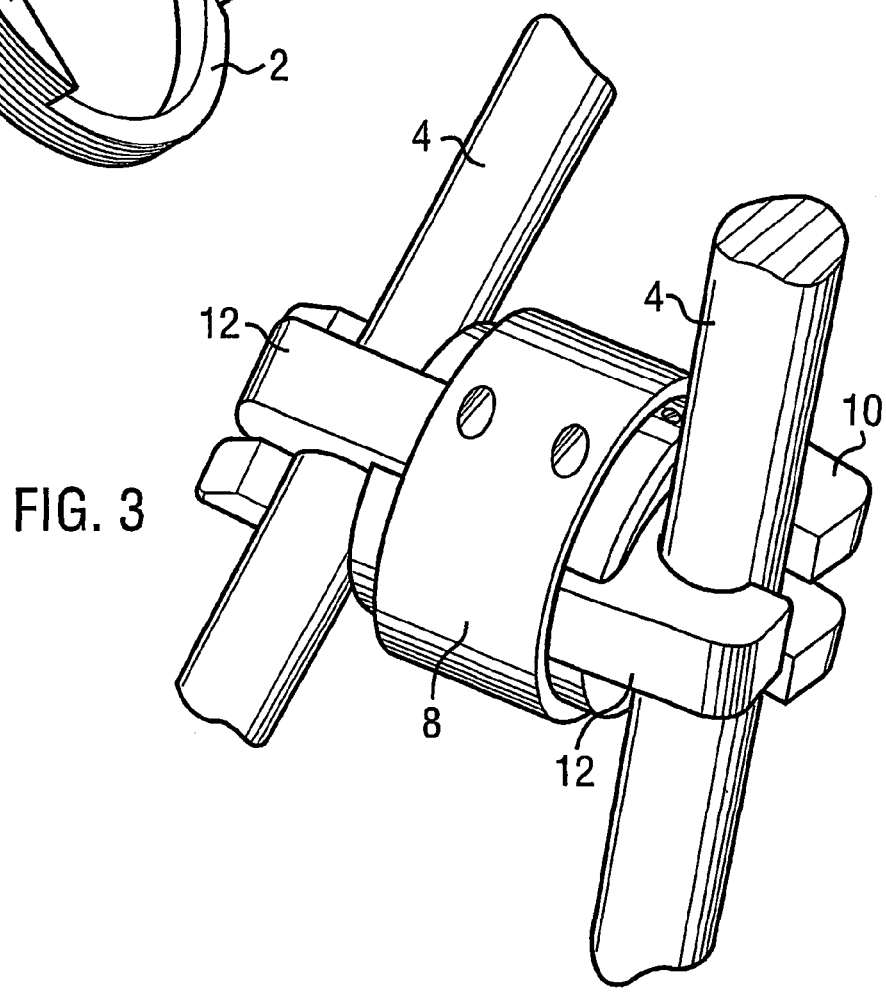
FIG. 3 is a perspective view of a gripping device according to a second embodiment of the invention with gripped elements held at either axial end.
Figure 4:
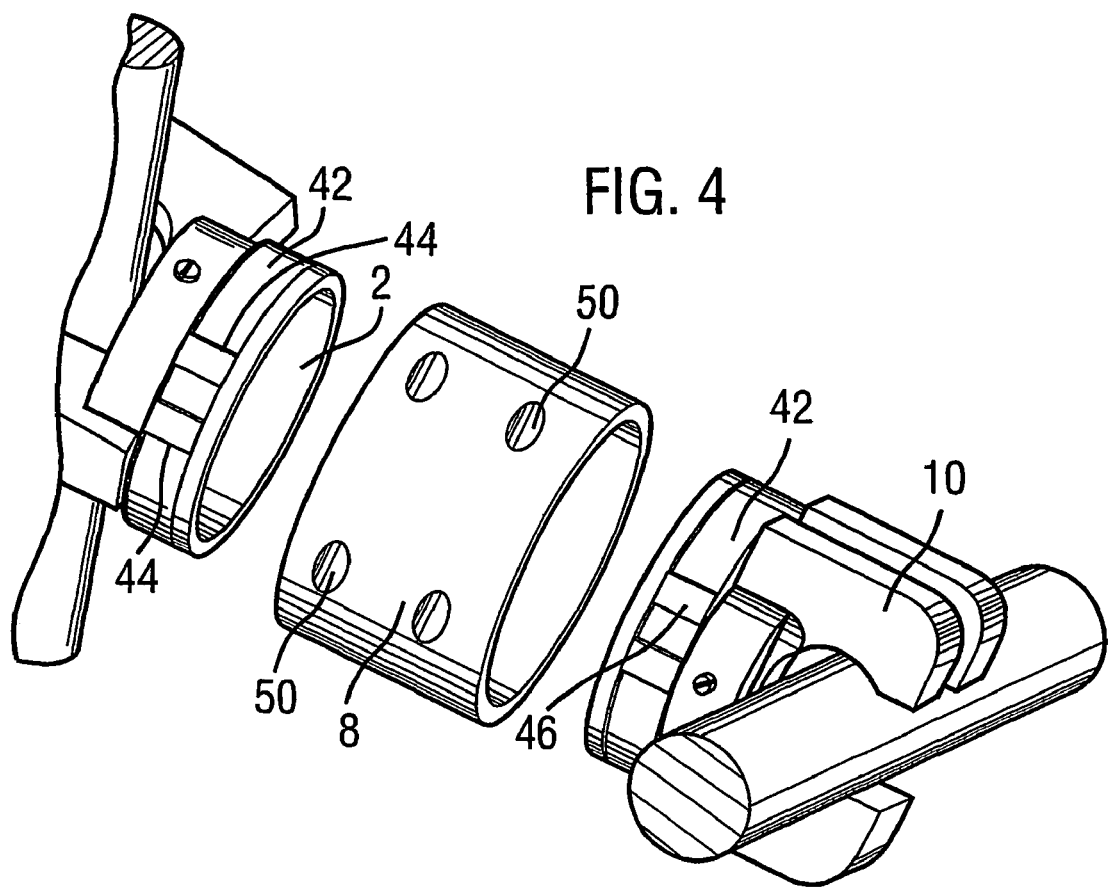
FIG. 4 is an exploded view of the device of FIG. 3.

The gripping device shown in FIG. 3 has two support bodies 2 mounted within a sleeve 8, with gripping elements 10 and 12 holding rods 4 at either axial end of the sleeve 8. This is essentially similar to the embodiment of FIGS. 1 and 2. However, as shown in FIG. 4 each support body has an annular outwardly directed groove which receives and supports a split collar 40. The split is defined between two jaws 42, which will be better appreciated from a review of FIG. 5. The jaw defines a ridge or wall and a flank surface 46 extending up to the wall 44 substantially tangentially to the collar periphery. The sleeve 8 is formed with a tangential passage, through which two pins 48 extend to engage the walls 44 on the collar 40. When the device is disassembled, for example in the form shown in FIG. 4, the natural resilience of the collar will expand it to go beyond the inner periphery of the sleeve 8. A simple gripping mechanism can be used to contract the collar to enable it to be inserted into the end of the sleeve 8 but of course, once the collar is fully confined within the sleeve, then an external mechanism cannot realistically be used. Accordingly, care is taken to locate the collar jaws 42 appropriately in the sleeve to ensure that pins 48 can make proper engagement as required. While once the support body 2 is properly received in the sleeve 8, the collar cannot be further adjusted in this manner, the urging of pins 48 towards each other in engagement with the respective walls 44, can of course contract the collar enabling the support body to be removed or at least moved axially against no more than a nominal resistance. This is of particular value if a device according to the invention, having served its purpose, is to be removed. However, the pins can also be used to partially contract the collar, and reducing the force required to translate the body in the sleeve. This is of particular value when the juxtaposed faces of the collar and outer sleeve are formed with annular grooves. The force required to move the body axially within the sleeve is of course considerably reduced if the collar is contracted to reduce the depth of the meshing engagement between the respective grooves.

Because the contraction of the collar 40 is only occasionally required, the pints 48 need not be a permanent component of the device illustrated. They can simply be pins operated (pressed towards each other) in the respective openings 50 formed in the sleeve. However, if needed they may be more permanent, and held in the openings 50 by means for example, of respective screw threads.

Although the device illustrated and described above is broadly circular in cross-section, it will be appreciated that many different cross-sections could be employed. The cross-section and dimensions can be specially selected to match the profile of the gripping elements 10 and 12, and of course the liner does not have to extend around substantially the entire periphery of the support body 2. Nevertheless, the circular profile illustrated is preferred.

Figure 5:
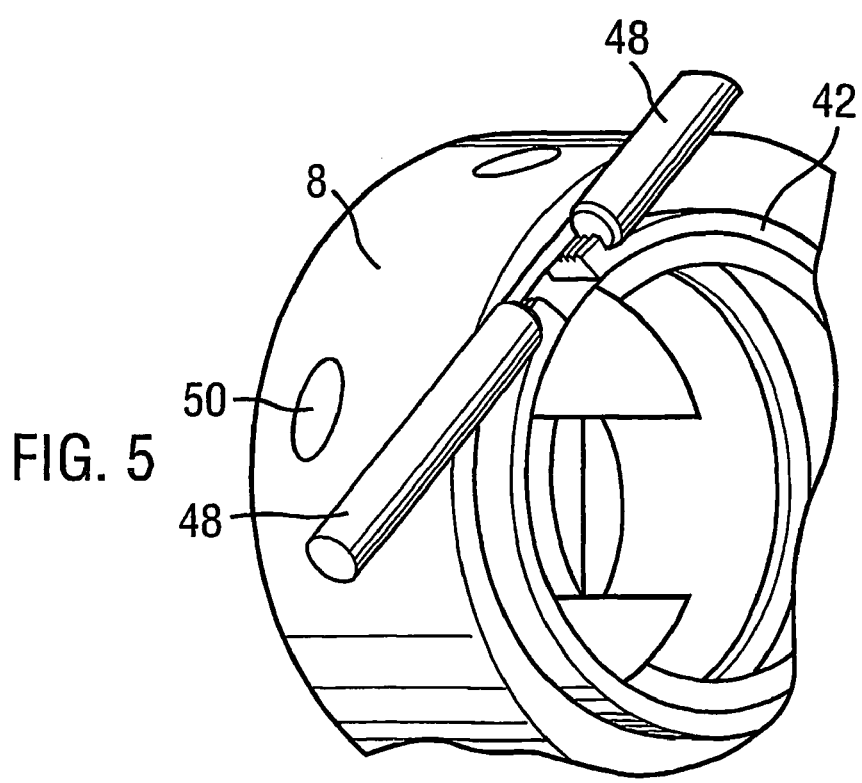
FIG. 5 is an enlarged sectional view showing the operation of an adjustment mechanism in a device of the kind shown in FIGS. 3 and 4.

As with the device of FIGS. 1 and 2, that of FIGS. 3 to 5 is very easily operated by squeezing items held between the gripping elements 10 and 12 together and forcing the respective support bodies 2 into the sleeve 8. As an alternative to manual operation, an electromagnetic mechanism can be used. This is of particular value when a plurality of devices must be operated substantially simultaneously. In these circumstances an appropriate electromagnetic unit can be coupled to each device and a common source of power whereby they can all be activated simultaneously when the respective relative orientation of bones to be fixed has been established.

Devices of the invention may be manufactured using any suitable materials having the requisite resilience or rigidity. Thus, one or more of the support body, sleeve and liner (if used) might be formed in a plastics material such as polythene or ABS, while other elements are formed in less flexible materials, such as stainless steels or aluminium alloys. Of course, the device may be formed wholly in the same material, metal or plastics, provided the construction or the material ensures the requisite resilience in the device as a whole.

The invention claimed is:

1. A gripping device for rods used in the external fixation of bones in surgical applications, the gripping device comprising:
   a sleeve;
   a pair of support bodies, each support body being disposed within and at either end of the sleeve, and mounted for translational movement along a common axis within the sleeve, each support body having a hollow interior with a pivot axle mounted therein; and
   a set of gripping elements pivotally mounted on the pivot axle in each support body, the pivot axle extending perpendicular to the common axis, the gripping elements each projecting from the interior of the respective support body and the respective ends of the sleeve and pivoting around the pivot axle and including laterally projecting lever arms in engagement with the sleeve end, whereby simultaneous movement of the support bodies towards each other within the sleeve and along the common axis causes working engagement of the lever arms with the sleeve ends such that the lever arms slide within the sleeve ends to simultaneously close the gripping elements at both ends of the sleeve.

2. The device according to claim 1 wherein the gripping element in each support body are mounted for pivotal movement about a common axis.

3. The device according to claim 2 wherein the gripping elements have matching jaws for gripping elongate components therebetween.

4. The device according to claim 3 wherein each support body has three gripping elements, two with jaws for engaging a component from one side at axially spaced sections therealong, and one with a jaw for engaging the component on the opposite side at a section between the spaced sections.

5. The device according to claim 1 wherein there is frictional contact between the external surface of each support body and the internal surface of the sleeve, which frictional contact holds each support body in place after translational movement.

6. The device according to claim 5 wherein the respective internal and external surfaces have peripheral teeth with one of the surfaces being resiliently flexible to allow the teeth on one surface to ride the teeth on the other surface during translational movement, but substantially locking the sleeve and support body axially in the absence of axial pressure.

7. The device according to claim 6 wherein the sleeve is formed as a split sleeve to provide resilient flexibility.

8. The device according to claim 1 wherein the working engagement is between the gripping element lever arms and the adjacent end face of the sleeve.

9. The device according to claim 1 wherein a liner is interposed between the inner surface of the sleeve and the juxtaposed outer surface of each support body, the liner being fixed axially to the support body and adjustable to selectively engage and hold support the body axially in the sleeve.

10. The device according to claim 9 wherein the selective engagement between each support body and the sleeve is resilient.

11. The device according to claim 9 wherein the liner comprises a split collar.

12. The device according to claim 11 wherein the collar is mounted in an annular groove on the support body and resiliently compressed by the sleeve making frictional engagement therewith.

13. The device according to claim 11 including an adjustment mechanism for enlarging or contracting the collar.

14. The device according to claim 13 wherein the juxtaposed surfaces of the sleeve and each support body are substantially cylindrical and the collar is annular, and wherein the adjustment mechanism comprises at least one pin extending tangentially through the wall of the sleeve and engaging the collar.

15. The device according to claim 14 wherein pins engage both ends of the split collar.

16. The device according to claim 9 wherein the juxtaposed surfaces of the liner and the sleeve are formed with complementary annular grooves which mesh resiliently to hold the support body axially in the sleeve.

17. The device according to claim 16 wherein the grooved surfaces are inclined saw tooth shaped in cross-section to permit axial movement of the support body in the sleeve overcoming their resilient engagement to enable translational movement to pivot the gripping elements.

* * * * *